US009085788B2

(12) United States Patent
Kanamarlapudi et al.

(10) Patent No.: US 9,085,788 B2
(45) Date of Patent: Jul. 21, 2015

(54) PROCESS FOR PREPARING AN ENANTIOMERICALLY ENRICHED, DEUTERATED SECONDARY ALCOHOL FROM A CORRESPONDING KETONE WITHOUT REDUCING DEUTERIUM INCORPORATION

(75) Inventors: Ramanaiah C. Kanamarlapudi, Bridgewater, NJ (US); Steven A. Weissman, Short Hills, NJ (US); Emerich Eisenreich, Claremont, CA (US); Xuejun Liu, Arcadia, CA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 74 days.

(21) Appl. No.: 13/820,003

(22) PCT Filed: Sep. 1, 2011

(86) PCT No.: PCT/US2011/050138
§ 371 (c)(1),
(2), (4) Date: Sep. 17, 2013

(87) PCT Pub. No.: WO2012/031072
PCT Pub. Date: Mar. 8, 2012

(65) Prior Publication Data
US 2014/0017739 A1    Jan. 16, 2014

Related U.S. Application Data

(60) Provisional application No. 61/379,182, filed on Sep. 1, 2010.

(51) Int. Cl.
*C12P 17/18*    (2006.01)
*C07B 59/00*    (2006.01)
*C07D 473/04*   (2006.01)

(52) U.S. Cl.
CPC ............. *C12P 17/182* (2013.01); *C07B 59/002* (2013.01); *C07D 473/04* (2013.01); *C12Y 101/01184* (2013.01)

(58) Field of Classification Search
CPC ..... C12P 17/182; C12P 17/18; C07B 59/002; C12Y 101/01184
USPC ........................................................ 435/119
See application file for complete search history.

(56) References Cited

U.S. PATENT DOCUMENTS

| 5,112,827 | A  | 5/1992  | Saunders et al. |
| 5,648,357 | A  | 7/1997  | Bianco et al. |
| 5,780,476 | A  | 7/1998  | Underiner et al. |
| 6,020,337 | A  | 2/2000  | Leigh et al. |
| 6,221,335 | B1 | 4/2001  | Foster |
| 6,316,458 | B1 | 11/2001 | Nadler et al. |
| 6,420,374 | B1 | 7/2002  | Bianco et al. |
| 6,440,710 | B1 | 8/2002  | Keinan et al. |
| 6,603,008 | B1 | 8/2003  | Ando et al. |
| 7,517,990 | B2 | 4/2009  | Ito et al. |
| 8,263,601 | B2 | 9/2012  | Tung et al. |
| 2005/0107420 | A1 | 5/2005 | Armstrong et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |
| 2008/0249089 | A1 | 10/2008 | Himmelsbach et al. |
| 2009/0239886 | A1 | 9/2009 | Tung et al. |
| 2011/0053961 | A1 | 3/2011 | Tung et al. |
| 2011/0059995 | A1 | 3/2011 | Tung et al. |
| 2011/0077255 | A1 | 3/2011 | Tung et al. |
| 2012/0202830 | A1 | 8/2012 | Tung et al. |
| 2013/0280768 | A1 | 10/2013 | Kanamarlapudi et al. |

FOREIGN PATENT DOCUMENTS

| EP | 0435152 A2 | 7/1991 |
| EP | 0435153 A2 | 7/1991 |
| WO | 87/00523 A2 | 1/1987 |
| WO | 94/22449 A1 | 10/1994 |
| WO | 95/26325 A2 | 10/1995 |
| WO | 9605854 A2 | 2/1996 |
| WO | 2005017135 A1 | 2/2005 |
| WO | 2007041630 A1 | 4/2007 |
| WO | 2007/118651 A1 | 10/2007 |
| WO | 2009045507 A2 | 4/2009 |
| WO | 2009/108375 A1 | 9/2009 |
| WO | 2009/108383 A2 | 9/2009 |
| WO | WO 2009/108375 A1 * | 9/2009 |
| WO | 2011/028835 A1 | 3/2011 |
| WO | 2011/028922 A1 | 3/2011 |

OTHER PUBLICATIONS

Pekala et al., Acta Poloniae Pharmaceutica vol. 64, No. 2, 109-113 (2007).*
Anderson, R.J., "Recent Advances and developments in the treatment of acute renal failure," Expert Opin. Ther. Patents,vol. (12), No. 5, pp. 645-655, 2002.

(Continued)

*Primary Examiner* — David J Steadman
(74) *Attorney, Agent, or Firm* — McCarter & English, LLP; Steven G. Davis; Emily Dertz

(57) ABSTRACT

The present invention provides a convenient and efficient process for the preparation of enantiomerically enriched, deuterated secondary alcohols without reducing deuterium incorporation.

23 Claims, No Drawings

(56) References Cited

OTHER PUBLICATIONS

Baillie, Thomas A., "The Use of Stable Isotopes in Pharmacological Research", Pharmacological Reviews, vol. 33, No. 2, pp. 81-132, 1981.
Browne, Thomas R., "Stable Isotope Techniques in Early Drug Development: An Economic Evaluation", J. Clin. Pharmacol, vol. 38, pp. 213-220, 1998.
Bursten, et al., "Lisofylline Causes Rapid and Prolonged Suppression of Serum Levels of Free Fatty Acids", The Journal of Pharmacology and Experimental Therapeutics, vol. 284, No. 1, pp. 337-345, 1997.
Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, pp. 653-657, 1987.
Cirillo, Pietro, et al., Systemic Inflammation, Metabolic Syndrome and Progressive Renal Disease, Nephrol Dial Transplant, 24:1384-1387, Feb. 10, 2009.
Davila-Esqueda, M.E., et al., Pentofxifyline Diminishes the Oxidative Damage to Renal Tissue Induced by Streptozotocin in the Rat, Experimental Diab. Res., 5:245-251, 2004.
Davis, et al., "Microbial models of mammalian metabolism: stereospecificaity of ketone reduction with pentoxifylline", Xenobiotica, vol. 15, No. 12, pp. 1001-1010, 1985.
Dyck, et al., "Effects of Deuterium Substitution on the Catabolism of ?-Phenylethylamine: An In Vivo Study", Journal of Neurochemistry, vol. 46, No. 2, pp. 399-404, 1986.
Ellermann, et al., Effect of pentoxifylline on the ischemic rat kidney monitored by 31P NMR spectroscopy in vivo, Biomed. Biochim. Acta, vol. 47, No. 6, pp. 515-521, 1988.
Fisher, et al., "The complexities inherent in attempts to decrease drug clearance by blocking sites of CYP-mediated metabolism," Current Opinion in Drug Discovery & Development, vol. 9, No. 1, pp. 101-109, 2006.
Foster, Allan B., "Deuterium isotope effects in studies of drug metabolism", TIPS, pp. 524-527, 1984.
Foster, Allan B., "Deuterium Isotope Effects in the Metabolism of Drugs and Xenobiotics: Implications for Drug Design", Advances in Drug Research, vol. 14, pp. 2-40, 1985.
Friese, Ryan S., et al, Matrix Metalloproteinases: Discrete Elevations in Essential Hypertension and Hypertensive end-Stage Renal Disease, Clin. Exp. Hypertens, 31(7):521-533: Oct. 2009.
Gouyette, et al., "Synthesis of Deuterium-labelled Elliptinium and its Use in Metabolic Studies", Biomedical and Environmental Mass Spectrometry, vol. 15, pp. 243-247, 1988.
Haskins, N.J., "The Application of Stable Isotopes in Biomedical Research", Biomedical Mass Spectrometry, vol. 9, No. 7, pp. 269-277, 1982.
Hewitson, Tim D., et al., Small Animal Models of Kidney Disease: A Review, Methods in Molecular Biology, 466:41-57, 2009.
Honma, et al., "Liberation of Deuterium from the Piperidine Ring during Hydroxylation", Drug Metabolism and Disposition, vol. 15, No. 4, pp. 551-559, 1987.
International Preliminary Report on Patentabilty issued in PCT Application No. PCT/US2009/001294 on Aug. 31, 2010.
International Preliminary Report on Patentabilty issued in PCT Application No. PCT/US2009/001305 on Aug. 31, 2010.
International Search Report issued in PCT Application No. PCT/US2009/001305 on Aug. 18, 2009.
International Search Report issued in PCT Application No. PCT/US2010/047574 on Oct. 14, 2010.
International Search Report issued in PCT Application No. PCT/US2010/047708 on Oct. 22, 2010.
International Search Report issued in PCT Application No. PCT/US2009/001294 on Jul. 8, 2009.
Kushner, et al., "Pharmacological uses and perspectives of heavy water and deuterated compounds", Can. J. Physiol. Pharmacol., vol. 77, pp. 79-88, 1999.
Latta, Paul P., Pat. App. Lexis 4112, Board of Patent Appeals and Interference, 5pp, Oct. 10, 2007.

Lee, et al., "Cytochrome P450 Isozymes Involved in Lisofylline Metabolism to Pentoxifylline in Human Liver Microsomes", Drug Metabolism and Disposition, vol. 25, No. 12, pp. 1354-1358, 1997.
Lillibridge, et al., "Metabolism of Lisofylline and Pentoxifylline in Human Liver Microsomes and Cytosol", Drug Metabolism and Disposition, vol. 24, No. 11, pp. 1174-1179, 1996.
Lin et al. "The Renoprotective Potential of Pentoxifylline in Chronic Kidney Disease," J. Chen. Med. Assoc. vol (68), No. 3, pp. 99-105, 2005.
Nicklasson et al., "Stereoselective Metabolism of Pentoxifylline In Vitro and In Vivo in Humans," Chirality 14:643-652 (2002).
Paap, et al., "Multiple-Dose Pharmacokinetics of Pentoxifylline and its Metabolites During Renal Insufficiency", The Annals of Pharmacotherapy, vol. 30, pp. 724-729, 1996.
Park, et al. "Metabolism of Fluorine-containing Drugs," Annu. Rev. Pharmacol. Toxicol. (41) 443-70 (2001).
Pieniaszek, et al., "Moricizine Bioavailablity via Simultaneous, Dual, Stable Isotope Administration: Bioequivalence Implications", The Journal of Clinical Pharmacology, vol. 39, pp. 817-825, 1999.
Raoul, et al., A Novel Drug Interaction Between the Quinolone Antibiotic Ciprofloxacin and a Chiral Metabolite of Pentoxifylline, Biochemical Pharmacology; 74:639-646 (2007).
Synfine Catalogue "1-(3-carboxypropyl) 3,7-dimethyl Xanthine-d6" listed in online catalogue dated Oct. 21, 2007; accessed at http://web.archive.org/web/20071021050610/http://synfine.com/products_details.cfm?autoid=605.
Synfine Catalogue "Hydroxy Pentoxifylline-d3" listed in online catalogue dated Oct. 21, 2007; accessed at http://web.archive.org/web/20071021050615/http://synfine.com/products_details.cfm?autoid=606.
Synfine Catalogue "Pentoxifylline-d3" listed in online catalogue dated Oct. 21, 2007; accessed at http://web.archive.org/web/20071021050605/http://synfine.com/products_details.cfm?autoid=604.
Tesch, Greg H., et al., Methods in Renal Research, Rodent Models of Streptozoticin-Induced Diabetic Nephropathy, Nephrology, 12:261-266, 2007.
Tonn, et al., Simultaneous Analysis of Diphenhydramine and a Stable Isotope Analog (2H10)Diphenhydramine Using Capillary Gas Chromatography with Mass Selective Detection in Biological Fluids from chronically Instrumented Pregnant Ewes, Biological Mass Spectrometry, vol. 22. 633-642, 1993.
Trental FDA label, Aventis Pharmaceuticals Inc., Apr. 2004.
Ward et al. "Pentoxifylline. A review of its pharmacodynamic and pharmacokinetic properties and its therapeutic effects", Drugs, vol. 34, pp. 50-97, 1987.
Wolen, Robert L., "The Application of Stable Isotopes to Studies of Drug Bioabailablity and Bioequivalence", The Journal of Clinical Pharmacology, vol. 26, pp. 419-424, 1986.
Written Opinion of the International Searching Authority issued in PCT/US2009/001294 dated Jul. 8, 2009.
Written Opinion of the International Searching Authority issued in PCT/US2009/001305 dated Aug. 18, 2009.
Wyska, et al. "Pharmacokinetic modeling of pentoxifylline and lisofylline after oral and intravenous administration in mice", Journal of Pharmacy and Pharmacology, vol. 59, pp. 495-501, 2007.
Buteau, Kristen C., Deuterated Drugs: Unexpectedly Nonobvious?, Journal of High Technology Law, X(1):22-74, 2009.
Magnusson, European Journal of Pharmacology 581 (2008) 290-295.
Cell Therapeutics Suffers on Lisofylline Trial Data, Cuts Development, http://www.thepharmaletter.com/file/20592/cell-therepeutics-suffers-on-lisofylline-trial-data-cuts-development.html, downloaded from the internet Aug. 9, 2011.
Forbes et al., Oxidative Stress as a Major Culprit in Kidney Disease in Diabetes, Diabetes, vol. 57, pp. 1446-1454 (2008).
Sweeney, The Open Critical Care Medicine Journal, 2010, 3, 7-19.
Moore, Jeffrey C., et al., Advances in the Enzymatic Reduction of Ketones, Acc. Chem. Res., 40:1412-1419, 2007.
Fronza, Giovanni, et al., Sterochemistry of the Double Bond Saturation in the Formation in Baker's Yeast of 4-(4-hydroxyphenyl)-2-butanone (Raspberry Ketone), Tetrahedron, 52(11):4041-4052, 1996.

(56) References Cited

OTHER PUBLICATIONS

Hammerschmidt, Friedrich, et al., Incorporation of D-[1-2H1]Glucose into 2-Aminoethylphosphonic Acid in Tetrahymena thermophila and into Fosfomycin in *Streptomyces fradia*.—The Sterochemical Course of a Phosphoenolpyruvate Mutase-Catalyzed Reaction, Liebigs Ann. Chem., pp. 1201-1203 (1992).

Kosjek, Birgit, et al., Preparative Asymmetric Syntehsis of 4,4-Dimethoxytetrahydro-2H-pyran-3-ol with a Ketone Reductase and in Situ Cofactor Recycling Using Glucose Dehydrogenase, Organic Process Research & Development, 12(4):584-588, 2008.

Schroer, Kirsten, et al., Process Intensification fo Substrate-Coupled Whole Cell Ketone Reduction by in Situe Acetone Removal, Organic Process Research & Development, 11(5):836-841, 2007.

Althouse, Victor E., et al., Asymmetric Reductions. XIII. Optically Active Benzyl-a-d Alcohol and n-Butyl-1-d Alcohol via Reductionby Actively Fermenting Yeast, Journal of the American Chemical Society, 88(15):3595-3599, Aug. 5, 1966.

Pekala, Elzbeita, et al., Alcohol Deydrogenases as Tools for the Preparation of Enantiopure Metabolites of Drugs with Methyl Alkyle Ketone Moiety, Scientia Pharmacetica, 77(1):9-17, 2009.

Pekala, Elzbeita, et al., Enantioselective Biotransformation of Pentoxifylline into Lisofylline Using Wine Yeast Biocatalysis, Acta Poloniae Pharmaceutica, 64(2):109-113, 2007.

Pekala, Elzbieta, et al., Enantioselective Reduction of Pentoxifylline to Lisofylline Using Whole-Cell *Lactobacillus* Kefiri Biotransformation, Biotechnology Journsal, 2(4):492-496, 2007.

Saishin Souyaku Kagaku (The Practice of Medicinal Chemistry), VI 1, p. 379, 1998.

Diabetic Nephropathy Treatment Overview, http://diabetes.webmd.com/tc/diabetic-nephropathy-treatment-overview, downloaded from the internet Jan. 16, 2013.

Written Opinion of the International Searching Authority issued in PCT/US2010/047574 dated Oct. 9, 2010.

Written Opinion of the International Searching Authority issued in PCT/US2010/047708 dated Oct. 9, 2010.

International Preliminary Report on Patentabilty issued in PCT Application No. PCT/US2010/047574 on Mar. 6, 2012.

International Preliminary Report on Patentabilty issued in PCT Application No. PCT/US2010/047708 on Mar. 6, 2012.

Bolick, D., Lisofylline, a Novel Antiinflammatory Compound, Protects Mesangial Cells from Hyperglycemia-and Angiotensin II-Mediated Extracellar Matrix Deposition, Endocrinology, 144(12): 5227-5231 (2003).

Kaluzna, et al., Ketereductases: Stereoselective Catalysts for the Facile Synthesis of Chiral Alcohols, Tetradhedron Asymmetry, Pergamom Press Ltd, 16(22):3682-3689, Nov. 14, 2005.

Davis, P.J., et al., Microbial Models for Mammalian Metabolism: Microbial Reduction and Oxidationo f Pentoxifylline, Applied and Environmental Microbiology, American Society for Microbiology, 48(2):327-331, Aug. 1, 1984.

Broussy, S., et al., Enatioselective, Ketoreductase-based Entry Int Pharmaceutical Building Blocks: Ethanol as Tunable Nicotinamide Reductant, Organic Letters, American Chemical Society, 11(2):305-308, Dec. 17, 2008.

* cited by examiner

PROCESS FOR PREPARING AN ENANTIOMERICALLY ENRICHED, DEUTERATED SECONDARY ALCOHOL FROM A CORRESPONDING KETONE WITHOUT REDUCING DEUTERIUM INCORPORATION

RELATED APPLICATION

This application is a 35 U.S.C. §371 national stage filing of International Application No. PCT/US2011/050138, filed on Sep. 1, 2011, which, in turn claims priority to U.S. Provisional Application No. 61/379,182, filed on Sep. 1, 2010. The entire contents of each of the foregoing applications are incorporated herein by reference in their entirety.

BACKGROUND OF THE INVENTION

The (R)M-1 metabolite of pentoxifylline is known as lisofylline and is known to have similar properties to pentoxifylline.

Deuterated (R) M-1 metabolites of pentoxifylline and related compounds have been reported as having therapeutic utility in WO2009/108383. There is a need for commercially feasible methods for producing such deuterated (R)-M-1 metabolites, as well as other deuterated (R)-alcohols.

SUMMARY OF THE INVENTION

Applicants have solved this problem by employing certain commercially available ketoreductases and carbonyl reductases to produce deuterated (R)-alcohols from the corresponding prochiral deuterated ketone in a highly stereoselective manner without loss of deuterium incorporation.

The present invention provides a process for the preparation of a compound of Formula I:

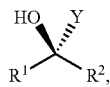

comprising reacting a compound of formula II:

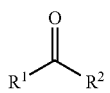

with a hydride source or a deuteride source in the presence of a ketoreductase or carbonyl reductase to form a compound of formula I with an enantiomeric excess of at least 80%, wherein:

Y is H when a compound of Formula II is reacted with a hydride source; or

Y is D when a compound of Formula II is reacted with a deuteride source;

$R^1$ is —$CH_3$ or —$CD_3$;

$R^2$ is a $C_2$-$C_{10}$ alkylene-X wherein X is H, D, or $R^3$ and the $C_2$-$C_{10}$ alkylene portion of $R^2$ is optionally substituted with a group independently selected from the group consisting of (i) one or more deuterium, and (ii) one $R^3$; and $R^3$ is (i) $C_6$-$C_{10}$ aryl, 5-10-membered heteroaryl, $C_3$-$C_8$ cycloalkyl, or saturated heterocyclyl, wherein $R^3$ is optionally substituted with one or more substituent independently selected from deuterium, $C_1$-$C_2$ alkyl optionally substituted with deuterium, and —OH; or (ii) a tautomer thereof;

wherein at least one of $R^1$ and the $C_2$-$C_{10}$ alkylene portion of $R^2$ is substituted with deuterium; and wherein the amount of deuterium incorporation at each deuterium in $R^1$ and the $C_2$-$C_{10}$ alkylene portion $R^2$ in the compound of formula I is substantially equal to the amount of deuterium incorporation at corresponding deuterium atoms in $R^1$ and $R^2$ in the compound of formula II.

The process of this invention is particularly useful to reduce deuterated forms of pentoxifylline to their corresponding deuterated alcohols.

DETAILED DESCRIPTION OF THE INVENTION

Definitions

"The term "alkyl" refers to a monovalent, saturated hydrocarbon group having the indicated number or range of carbon atoms. For example, $C_2$-$C_{10}$ alkyl is an alkyl having from 2 to 10 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl, 2-methylpentyl and heptyl.

The term "cycloalkyl" refers to a monovalent monocyclic or bicyclic saturated group containing only carbon ring atoms. The term "$C_3$-$C_8$ cycloalkyl" refers to a monocyclic saturated group containing between 3 and 7 carbon ring atoms. Examples of cycloalkyl include cyclopropyl, cyclobutyl, cyclopentyl, and cyclohexyl, cycloheptyl, cis- and trans-decalinyl, and norbornyl.

The term "aryl" refers to an aromatic carbocycle. The term "$C_6$-$C_{10}$ aryl" refers to a monocyclic or bicyclic, aromatic carbocycle containing between 6 and 10 ring carbon atoms. Examples of aryl are phenyl and naphthyl.

The term "saturated heterocyclyl" refers to a monovalent monocyclic or bicyclic saturated group containing between 3 and 8 ring atoms, wherein one or more ring atoms is a heteroatom independently selected from N, O, and S. Examples of saturated heterocycles include azepanyl, azetidinyl, aziridinyl, imidazolidinyl, morpholinyl, oxazolidinyl, piperazinyl, piperidinyl, pyrazolidinyl, pyrrolidinyl, tetrahydrofuranyl, and thiomorpholinyl.

The term "heteroaryl" refers to a monovalent monocyclic or bicyclic aromatic group, wherein one or more ring atoms is a heteroatom independently selected from N, O, and S. A 5-10 membered heteroaryl is a monocyclic or bicyclic heteroaryl that contains between 5 and 10 ring atoms. Examples of heteroaryl groups include furanyl, thiazolyl, isothiazolyl, isoxazolyl, oxazolyl, pyrimidinyl, pyrazolyl, pyridazinyl, pyridinyl, pyrrolyl, thiadiazolyl, thiophenyl, triazinyl, triazolyl, quinolinyl, quinazinyl, indolyl, isoindolyl, 3,7-dihydro-1H-purine-2,6-dion-yl; xanthinyl, hypoxanthinyl, theobrominyl, uric acid, isoguaninyl, thymine, and uracilyl.

The term "ketoreductase or carbonyl reductase" refers to an enzyme belonging to Enzyme Classification Class 1.1.1.184, which, in the presence of which a hydride source, is capable of converting a methyl ketone into a secondary alcohol. The term "methyl ketone" refers to a ketone of the formula:

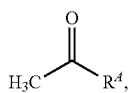

wherein $R^4$ is $C_nH_{2n+1}$ and n is an integer between 2 and 10.

The term "substituted" refers to the replacement of one or more hydrogen atoms with the indicated substituent. For avoidance of doubt, substitutions may occur on the terminus of a moiety. For example, the terminal —$CH_3$ group on $R^2$ may be substituted with an $R^3$. "Substituted with deuterium" refers to the replacement of one or more hydrogen atoms with a corresponding number of deuterium atoms.

When a position is designated specifically as "D" or deuterium, the position is understood to have deuterium at an abundance that is at least 1000 times greater than the natural abundance of deuterium, which is 0.015% (i.e., at least 15% incorporation of deuterium). In certain embodiments, when a position is designated as "D" or deuterium that position has at least 50.1% incorporation of deuterium, at least 75% incorporation of deuterium; at least 80% incorporation of deuterium, at least 85% incorporation of deuterium; at least 90% incorporation of deuterium; at least 95% incorporation of deuterium; at least 98% incorporation of deuterium; at least 99% incorporation of deuterium; or at least 99.5% incorporation of deuterium.

When a position is designated specifically as "H" or hydrogen, the position is understood to have hydrogen at its natural isotopic abundance.

The amount of deuterium incorporation at a deuterium atom in a compound of Formula I is said to be "substantially equal" to the amount of deuterium incorporation at the corresponding deuterium atom in a compound of Formula II if the difference in the amount of deuterium incorporation between them is no more than about 5%, as an example no more than about 3%; no more than about 2%; no more than about 1%; or no more than about 0.5%.

Ketones Useful as Compounds of Formula II

It will be understood that each of $R^1$ and $R^2$ in a compound of Formula I,

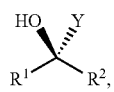

(I)

is structurally identical to the corresponding $R^1$ and $R^2$ in a compound of Formula II,

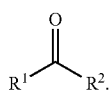

(II)

Notwithstanding this, according to the present invention, the amount of deuterium incorporation at any deuterium present in $R^1$ and $R^2$ of a compound of Formula I is substantially equal to the amount of deuterium incorporation at the corresponding deuterium atoms in a compound of Formula II.

In one embodiment, $R^2$ is substituted with one or two $R^3$.

In one embodiment, at least one of $R^1$ and $R^2$ comprises a deuterium bound to the carbon atom adjacent the carbonyl carbon.

In one embodiment, each of $R^1$ and $R^2$ is substituted with one or more deuterium. In one aspect of this embodiment at least one of $R^1$ and $R^2$ comprises a deuterium bound to the carbon atom adjacent the carbonyl carbon.

In one embodiment, $R^1$ is $CH_3$.

In another embodiment, $R^1$ is $CD_3$.

In one embodiment, $R^2$ is $C_2$-$C_6$ alkyl optionally substituted with one or more deuterium and optionally substituted with one or two $R^3$. In one aspect of this embodiment, $R^2$ is —$CH_2$—($C_1$-$C_5$ alkyl optionally substituted with one or more deuterium and optionally substituted with one $R^3$. In another aspect of this embodiment, $R^2$ is —$CH_2$—($C_1$-$C_5$ alkyl optionally substituted with one or more deuterium and optionally substituted with one $R^3$).

In one embodiment, $R^3$ is (i) 5-10-membered heteroaryl optionally substituted with one or more substituents independently selected from deuterium, $C_1$-$C_2$ alkyl optionally substituted with deuterium, and —OH; or (ii) a tautomer thereof.

In one embodiment, a compound of Formula II has structural Formula II-A:

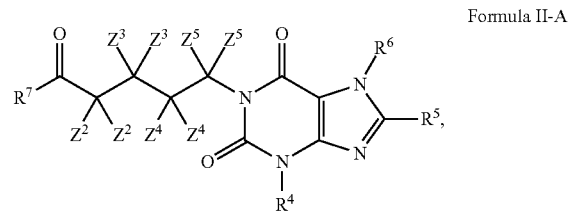

Formula II-A or a salt thereof, wherein:
each of $R^4$, $R^6$ and $R^7$ is independently selected from —$CH_3$ and —$CD_3$;
$R^5$ is hydrogen or deuterium or a combination thereof;
each $Z^2$ is the same and is hydrogen or deuterium;
each $Z^3$ is the same and is hydrogen or deuterium;
each $Z^4$ is the same and is hydrogen or deuterium;
each $Z^5$ is the same and is hydrogen or deuterium; and
either $R^7$ is —$CD_3$ or at least one of $Z^2$, $Z^3$, $Z^4$ and $Z^5$ is deuterium. In such an embodiment, the corresponding compound of Formula I has structural Formula I-A:

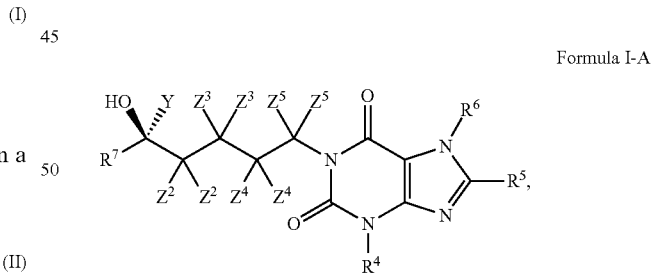

Formula I-A wherein $R^4$, $R^5$, $R^6$, $R^7$, $Z^2$, $Z^3$, $Z^4$ and $Z^5$ are as defined for Formula II-A; and Y is as defined for Formula I.

In one embodiment of Formula I-A and II-A, each $R^7$ is —$CD_3$.

In one embodiment of Formula I-A and II-A, each $Z^2$ is deuterium.

In another embodiment of Formula I-A and II-A, each $Z^2$ is hydrogen.

In one embodiment of Formula I-A and II-A, each $R^5$ is deuterium.

In one embodiment of Formula I-A and II-A, each $R^5$ is hydrogen.

In one embodiment of Formula I-A and II-A, each $Z^3$, $Z^4$ and $Z^5$ is hydrogen. In one aspect of this embodiment each $R^6$ is —$CH_3$ and each $R^7$ is —$CD_3$. In a more specific aspect, each $R^4$ is —$CH_3$, each $R^6$ is —$CH_3$; and each $R^7$ is —$CD_3$. In another aspect of this embodiment each $R^6$ is —$CD_3$ and each $R^7$ is —$CD_3$.

In one embodiment of Formula I-A and II-A, each $Z^3$, $Z^4$ and $Z^5$ is deuterium.

In one embodiment of Formula I-A and II-A, each $R^6$ and each $R^4$ is —$CD_3$.

In one embodiment of Formula II-A, the compound is selected from any one of:

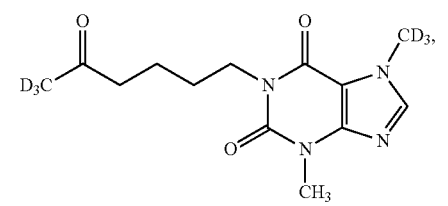

99

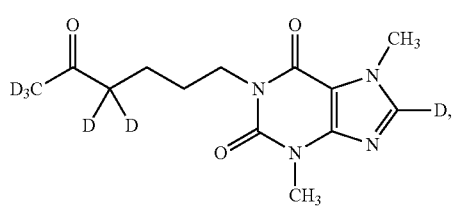

407

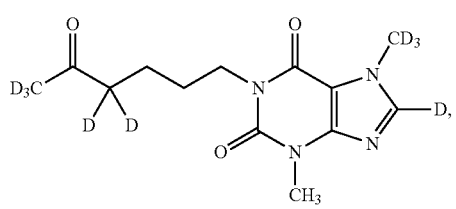

409

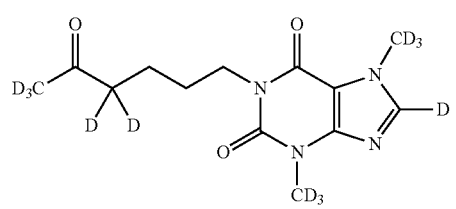

413

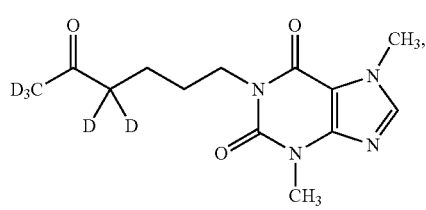

107

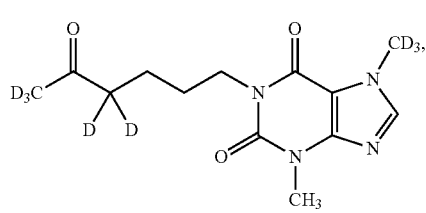

109

-continued

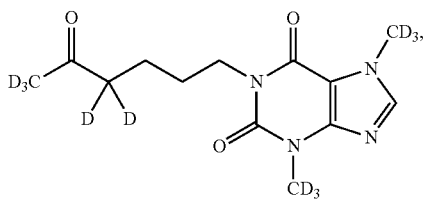

113

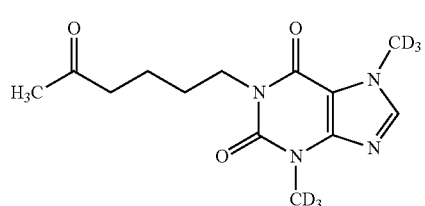

101

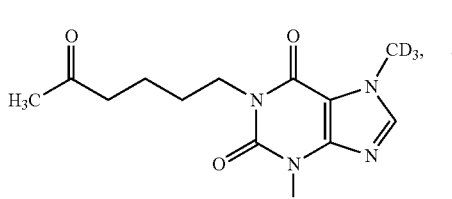

100, and

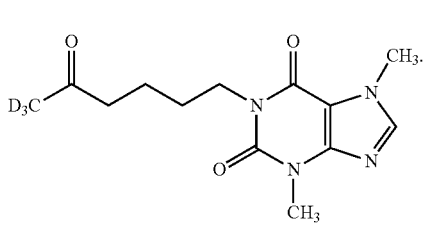

157

In one embodiment of Formula I-A, the compound is selected from the following:

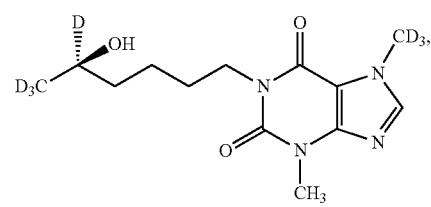

154(R)

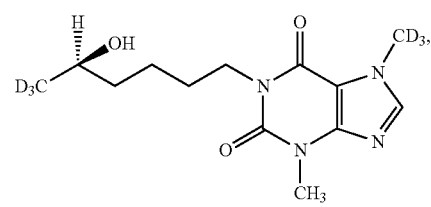

155(R)

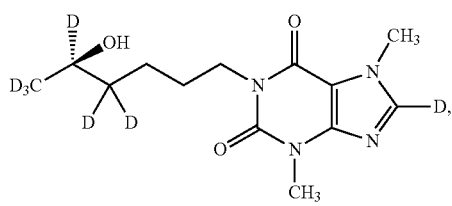

437(R)

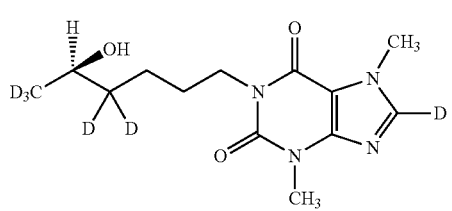
421(R)
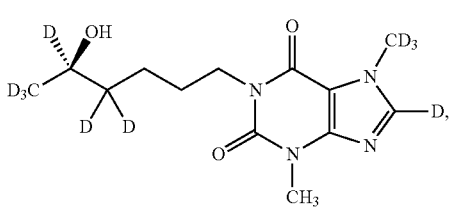
435(R)
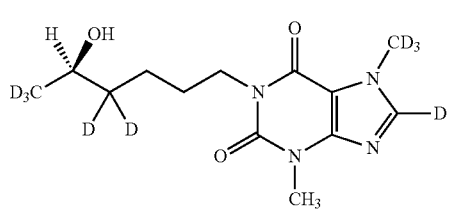
419(R)
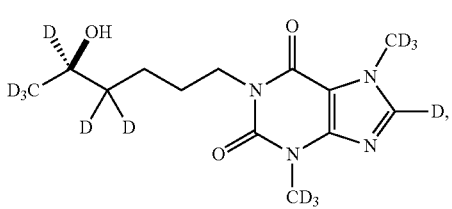
434(R)
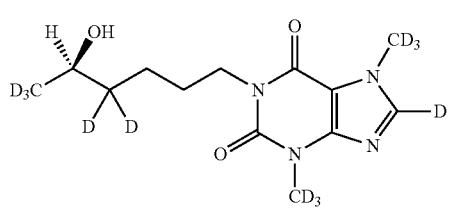
418(R)
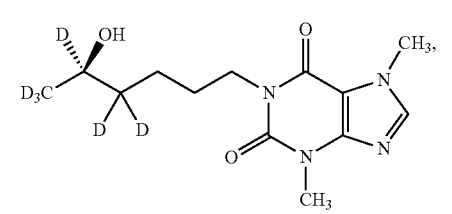
137(R)
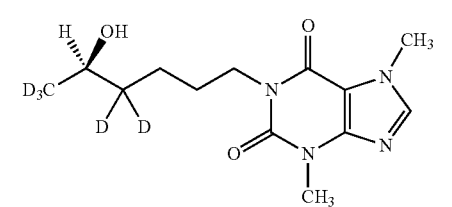
121(R)
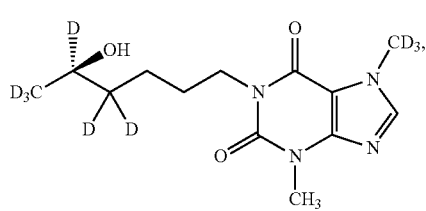
135(R)
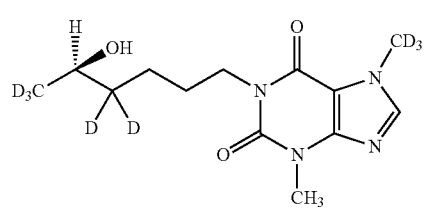
119(R)
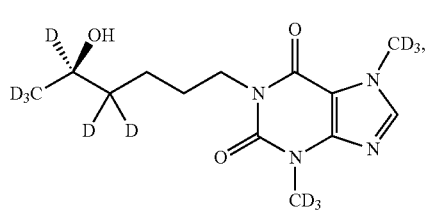
134(R)
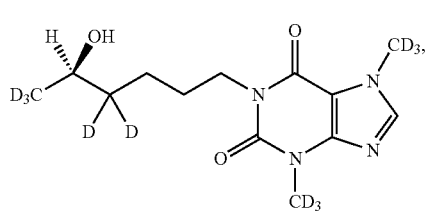
118(R)
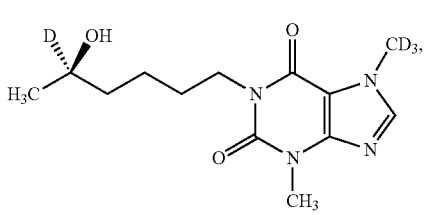
131(R)
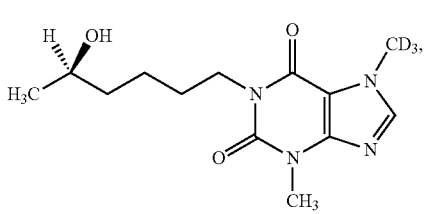
116(R)
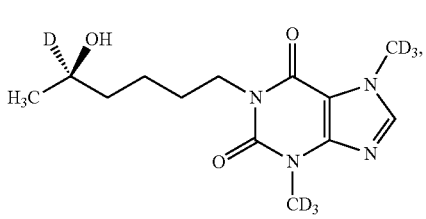
130(R)

-continued 115 (R)

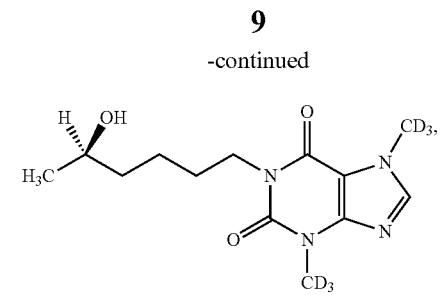

156 (R) and

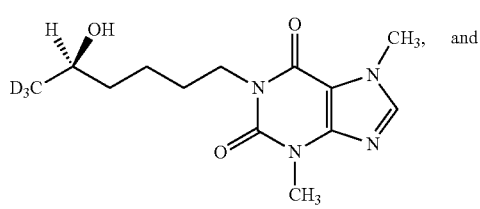

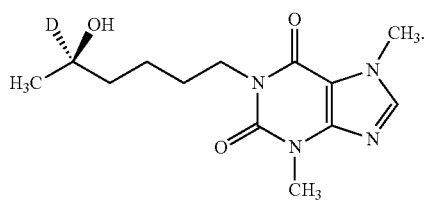

In one specific aspect, the compound of Formula II-A is

407

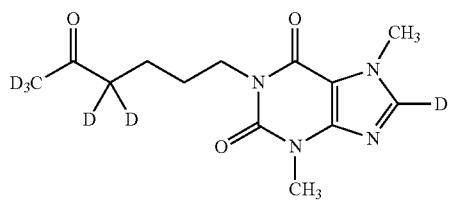

(Compound 407) and the compound of Formula I-A is

437(R)

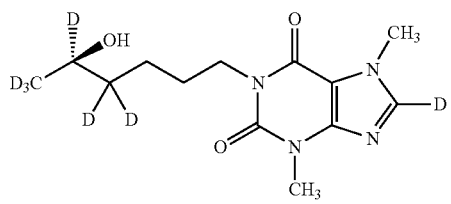

(Compound 437(R)).

In one embodiment, Compound 437 (R) is further converted to Compound 137(R) by treatment with $K_2CO_3$ and water. Thus, maintenance of the deuteration at that position during the enzymatic conversion to Compound 437(R) is unimportant:

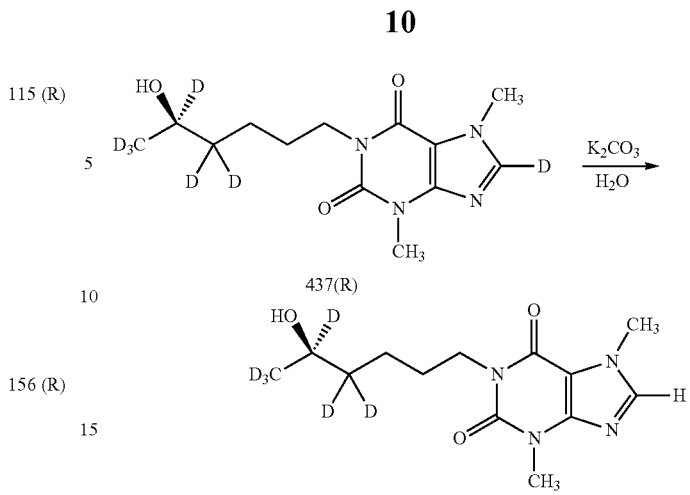

In one embodiment, compound 137(R) is substantially free of 437(R). "Substantially free" means that the amount of 437(R) is equal to or less than 5%, more preferably equal to or less than 1%, or more preferably equal to or less than 0.1%, of the amount of 137(R).

In one embodiment, any compound of formula I-A having a group

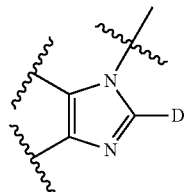 [SMILES: *c1ncn(*)c1*]

may be further converted to a compound having the same structure except for having a group

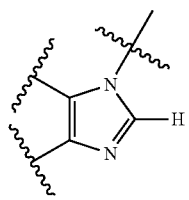

by treating with a suitable base and a proton source, such as water.

Applicants have discovered that the use of a ketoreductase or carbonyl reductase to reduce a deuterium-containing ketone compound of Formula II, in particular a compound of Formula II-A, allows for both high enantiomeric enrichment and substantially no loss of deuterium incorporation. In particular, the amount of deuterium incorporation at each deuterium in $R^1$ and $R^2$ in the compound of formula I is substantially equal to the amount of deuterium incorporation at corresponding deuterium atoms in $R^1$ and $R^2$ in the compound of formula II. This is particularly surprising in that it was unexpected that one could provide buffer conditions that (1) allowed the ketoreductase or carbonyl reductase to efficiently reduce the ketone without also allowing the enzyme to catalyze deuterium-to-hydrogen exchange on the existing deuterium atoms; (2) would not result in an acidic pH which would be expected to cause deuterium-to-hydrogen exchange on the existing deuterium atoms; and (3) would not require for activity sufficiently basic or acidic conditions that would also be expected to cause deuterium-to-hydrogen exchange.

In a related embodiment the invention provides a method of making Compound 133(R)

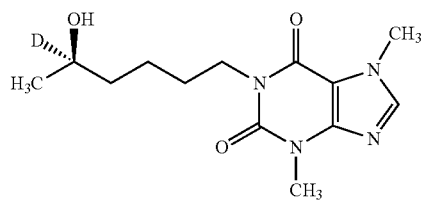

133(R)

comprising the step of reacting pentoxifylline:

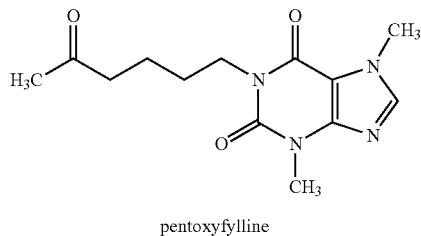 [SMILES: CC(=O)CCCCn1c(=O)c2c(ncn2C)n(C)c1=O]

pentoxyfylline with a deuteride source in the presence of a ketoreductase or carbonyl reductase and an appropriate catalytic co-factor at a pH between 6.5 and 7.3 to form a compound of formula I with an enantiomeric excess of at least 90% and deuterium incorporation of at the hydroxy carbon of Compound 133(R) of least 90%.

Any ketoreductase or carbonyl reductase that produces a 90% or greater enantiomeric excess of the (R)—OH stereoisomer of Formula II may be utilized in the method of this invention. Commercially available kits containing different ketoreductases or carbonyl reductases are available from multiple vendors. A determination of whether or not a particular ketoreductase or carbonyl reductase produces a 90% or greater enantiomeric excess of the (R)—OH stereoisomer of Formula II may be achieved by standard techniques well-known in the art. For example, a compound of Formula II may be incubated with the ketoreductase or carbonyl reductase to be screened in the presence of a hydride or deuteride source.

In one embodiment, the ketoreductase is a naturally occurring ketoreductase selected from the group consisting of *Candida magnoliae* ketoreductase, *Candida parapsilosis* ketoreductase, and *Sporobolomyces salmicolor* ketoreductase.

In one embodiment, the ketoreductase or carbonyl reductase is selected from any one or ALMAC Carbonyl Reductases CRED A161, CRED A291, CRED A311, or CRED A601 (each commercially available from ALMAC Group Ltd, Craigavon, England), any one of CODEXIS Ketoreductases KRED-NADP-118, or KRED-NAD 1110 (each commercially available from Codexis Inc., Redwood City, Calif.), or SYNCORE Ketoreductases ES-KRED-120, ES-KRED-126, or ES-KRED-131 (each commercially available from Syncore Labs, Shanghai, China). In one aspect of this embodiment, the enzyme is selected from CRED A291, CRED A311, or CRED A601. In a more specific aspect, the enzyme in CRED A311.

In one embodiment, the amount of enzyme used in the reaction ranges from 0.05 wt % to 10 wt % as a percentage of the weight of the substrate, such as 0.5 wt % to 5 wt %. In one embodiment, the amount of enzyme is between 1.0 wt % and 2.0 wt %. In a more specific aspect, the amount of enzyme is about 1.0 wt %.

In one embodiment, the compound of formula I is formed with an enantiomeric excess of at least 90%. In one aspect of this embodiment, the enantiomeric excess is at least 94%. In a more particular aspect of this embodiment, the enantiomeric excess is at least 96%. In a more particular aspect of this embodiment, the enantiomeric excess is at least 98%.

The process of this invention requires the presence of a hydride source or a deuteride source. The term "hydride source" refers to a compound or mixture that is capable of providing a hydride anion or a synthetic equivalent of a hydride anion. Similarly, the term "deuteride source" refers to a compound or mixture that is capable of providing a deuteride anion or a synthetic equivalent of a deuteride anion. A hydride or deuteride source comprises a co-factor, which may be in catalytic or stoichiometric amounts. When the co-factor is in a catalytic amount, the hydride or deuteride source comprises a co-factor regeneration system.

A co-factor used with the ketone reductase or carbonyl reductase in the process of this invention is selected from NAD, NADP, NADH, NADPH, NAD$^2$H and NADP$^2$H. The choice of co-factor may be based upon (a) the presence or absence of a co-factor regeneration system; (b) the requirement for a hydride versus a deuteride source; and (c) compatibility with the specific ketone reductase or carbonyl reductase employed. In embodiments where the hydride or deuteride source does not comprise a co-factor regeneration system, the co-factor is in a stoichiometric amount and is a reduced co-factor which is therefore selected from NADH and NADPH for a hydride source, or NAD$^2$H and NADP$^2$H for a deuteride source. It is well known in the art—or information is available from the commercial supplier of the specific ketone reductase or carbonyl reductase—whether NADH or NADPH is the appropriate co-factor for a given ketone reductase or carbonyl reductase. In this embodiment, the reduced co-factor is present in stoichiometric amounts as compared to the compound of Formula II.

In another embodiment, the hydride or deuteride source additionally comprises a co-factor regeneration system. The high cost of co-factors, in particular the deuterated co-factors, makes their use on a stoichiometric basis impractical. A low-cost co-factor regeneration system continually produces and regenerates the reduced form of the co-factor, requiring the co-factor to be present in only catalytic amounts. Moreover, the use of a co-factor regeneration system eliminates the need to use a reduced co-factor or a deuterated co-factor. The co-factor regeneration system produces the required reduced or reduced and deuterated co-factor in situ. Accordingly, any cofactor or combinations of cofactors compatible with the chosen ketone reductase or carbonyl reductase can be employed with a co-factor regeneration system. In this embodiment, therefore, NAD is interchangeable with NADH and NAD$^2$H; and NADP is interchangeable with NADPH and NADP$^2$H. Similarly, the designations "-NAD" and "-NADH", and "-NADP" and "-NADPH", respectively, are used interchangeably herein in conjunction with enzymes that use, respectively, NADH and NADPH as co-factors.

When used in conjunction with a co-factor regeneration system the amount of co-factor can range from 0.1 wt % to 5 wt %. In one aspect of this embodiment, the amount of cofactor is between 1 wt % and 3 wt %. In an alternate aspect of this embodiment, the amount of cofactor is between 0.1 wt % and 1.1 wt %.

A typical co-factor regeneration system consists of a dehydrogenase and a substrate for that dehydrogenase. Without being bound by theory or mechanism, Applicants believe that upon catalysis by the dehydrogenase, its substrate provides a hydride or deuteride anion to regenerate (reduce) the cofactor. The newly reduced cofactor can then subsequently donate a hydride or deuteride atom to the compound of Formula II to provide a compound of Formula I. In certain embodiments, the substrate for the dehydrogenase may be generated in situ from the corresponding ketone and a reducing agent. A second co-factor regeneration system takes advantage of the fact that certain ketoreductases and carbonyl reductases both possess alcohol dehydrogenase activity. In this system an alcohol dehydrogenase substrate is used and upon catalysis donates the hydride or deuteride ion to the co-factor.

Examples of hydride cofactor regeneration systems include, but are not limited to, reducing sugars and their corresponding hydrogenase, e.g., glucose and glucose dehydrogenase ("GDH"), glucose-6-phosphate and glucose-6-phosphate dehydrogenase, etc.; formate and formate dehydrogenase; a secondary (e.g., isopropanol) alcohol and a secondary alcohol dehydrogenase; phosphite and phosphite dehydrogenase; molecular hydrogen and hydrogenase; and ethanol, aldehyde dehydrogenase and an alcohol dehydrogenase.

Examples of deuteride co-factor regeneration systems include, but are not limited to, deuterated reducing sugars and their corresponding dehydrogenase, e.g., deuterated glucose and GDH, deuterated glucose-6-phosphate and glucose-6-phosphate dehydrogenase, etc.; deuterated formate and formate dehydrogenase; a secondary deuterated (e.g., deuterated isopropanol) alcohol alone or together with a secondary alcohol dehydrogenase; deuterated phosphite and phosphite dehydrogenase; molecular deuterium and hydrogenase; and deuterated ethanol and aldehyde dehydrogenase optionally together with an alcohol dehydrogenase.

In one embodiment of the process, the deuteride co-factor regeneration system comprises a substrate having a —C(D)OH functional group and its associated dehydrogenase. In a related embodiment, the substrate having a —C(D)OH functional group is generated in situ. In this related embodiment, the deuteride co-factor regeneration system comprises (a) a compound having a C=O functional group; (b) a metal deuteride or a mixed metal deuteride, such as a borodeuteride or aluminum deuteride of a metal such as sodium or lithium, capable of reducing the C=O functional group to a —C(D)OH functional group; and (c) a dehydrogenase that acts upon the —C(D)OH functional group. As an example, the substrate having a —C(D)OH functional group is a $C_1$-$C_6$ alcohol such as $CH_3C(D)(OH)CH_3$. As another example, the substrate having a —C(D)OH functional group is carbohydrate of the formula $C_6H_{11}DO_6$, such as deuterated glucose (shown below in its open chain and pyranose forms):

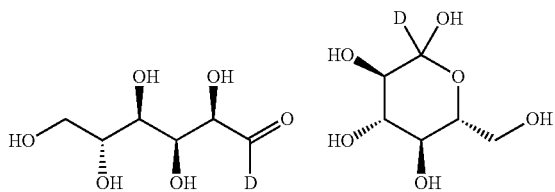 [SMILES: [2H]C(=O)[C@H](O)[C@@H](O)[C@H](O)[C@H](O)CO ; [2H]C1(O)O[C@H](CO)[C@@H](O)[C@H](O)[C@H]1O]

As yet another example the deuterated glucose is generated in situ from D-glucono-δ-lactone and $NaBD_4$. This embodiment is advantageous in that an otherwise expensive deuterated glucose substrate is generated in situ from relatively inexpensive D-glucono-δ-lactone and $NaBD_4$.

Moreover, the inventors have discovered that the use of deuterated glucose (or D-glucono-δ-lactone and $NaBD_4$) as part of the deuteride source consistently produced high deuterium incorporation (>90%) at the Y position of a compound of Formula I and in particular a compound of Formula I-A. The use of deuterated glucose in the deuteride source in the production of

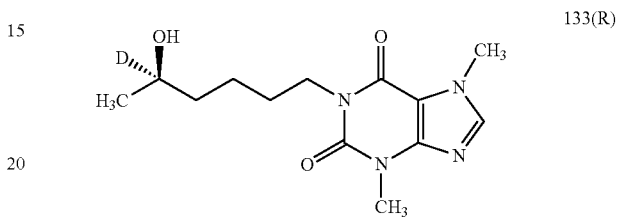

from pentoxifylline:

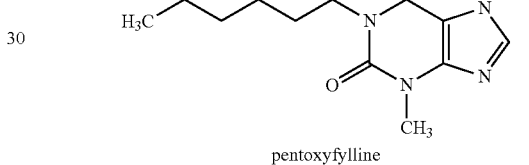

pentoxyfylline in accordance with this invention will also result in a surprisingly high deuterium incorporation at the indicated position of Compound 133(R).

When a combination of (a) GDH, glucose and a co-factor; (b)(i) GDH, deuterated glucose and a cofactor; or (b)(ii) GDH, D-glucono-δ-lactone, a metal deuteride or a mixed metal deuteride, and a cofactor is used as (a) the hydride source or (b) the deuteride source, respectively, the amount of GDH in the reaction can range from 0.01 wt % to 5 wt %. The term "wt %" means the amount of substance that is the recited percent of the amount of substrate present on a wt/wt basis. In one embodiment, the amount of GDH is between 0.05 wt % and 0.15 wt %. In an alternate embodiment, the amount of GDH is between 0.1 wt % and 0.2 wt %.

An appropriate pH to perform the method according to the present invention means buffer conditions that maintain the pH at between 6.0 and 7.5 throughout the reaction. In one embodiment, the pH of the reaction was maintained at between 6.5 and 7.3. In another embodiment, the pH of the reaction was maintained between 6.0 and 7.0. Typically dropwise addition of KOH is used to maintain the desired pH because the enzymatic reaction generates acid. In one aspect, the pH of the reaction is maintained between 6.90 and 7.05. If the pH of the reaction is allowed to drop below the desired range, the enzyme will typically become irreversibly inactivated and the compound of Formulae I and II subject to acid-catalyzed deuterium-to-hydrogen exchanged.

In one embodiment of the process of the invention, the process is performed at a temperature of about 20° C. to 37° C. In one aspect of this embodiment, the temperature is about 29° C. to 32° C.

In one embodiment of the process of the invention, the process is performed over a time period of about 12 hours to about 24 hours. In one embodiment, the time period is about 24 hours to about 40 hours. In one embodiment, the time period is about 40 hours to about 72 hours. In one embodiment, the time period is a time period sufficient for less than about 5% of the initial amount of compound of formula (II) to be present.

Example 1

Preparation of Compound 407

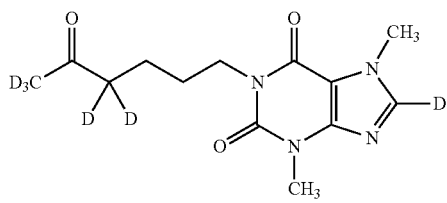
(407)

In a 50-L Jacket Glass Reactor, pentoxifylline (900 g) was reacted with deuterium oxide (99% of "D", 2.7 L) in the presence of potassium carbonate (0.25 equiv) in toluene (18 L) at 85-87° C. (refluxing) over four hours. The reaction mixture was cooled to 55° C. and the agitation was stopped to allow the layers to separate. The reaction mixture was held overnight at 55° C. $^1$H NMR analysis of an IPC sample of the organic layer showed the deuterium incorporation was 94.4% "D" at the methyl position. The bottom aqueous layer was collected. Following the same exchange conditions, a second exchange was conducted with a solution of potassium carbonate (0.25 equiv) in deuterium oxide (99% of "D", 2.7 L). After separation, a third exchange was conducted with a solution of potassium carbonate (0.25 equiv) in deuterium oxide (99.8% of "D", 2.7 L). $^1$H NMR analysis of an IPC sample of the organic layer showed the deuterium incorporation was 99.6% "D" at the methyl position after three exchanges. The organic layer was concentrated to ca. 5.5 L (6 vol) at 60° C. (Batch temperature) and cooled slowly. The solids were formed at 36° C. and n-heptane (1.8 L) was added to form a thin slurry. The slurry was stirred at 25° C. over the weekend and filtered to provide white solids (825 g, wet). The solids were dried in vacuum oven (28.5 inch Hg) at 45-48° C. over night to afford Compound 407 (778.5 g, 84.6% yield). $^1$H NMR analysis of Compound 407 showed that the deuterium incorporation was 99.7% "D" at the methyl position. An HPLC purity check by area showed that the purity was 99.96%.

Example 2

Screening of Carbonyl Reductases and Ketoreductases

ALMAC Carbonyl Reductases

The ability of the 40 individual carbonyl reductases in the ALMAC Carbonyl Reductase (CRED) Screening Kit to convert Compound 407 to Compound 421(R)

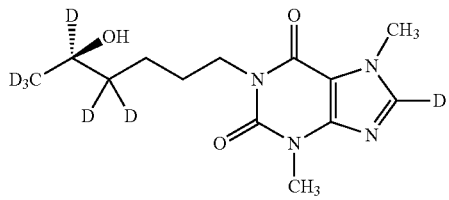
421(R)

was tested as follows:

Into a vial was added 1 mL of a 15 mg/mL solution of the CRED to be tested in 0.1M K$_2$HPO$_4$, pH 7.0. To that vial was added 100 μL of a 300 mg/mL solution of glucose; 100 μL of a 10 mg/mL solution of the appropriate co-factor NAD or NADP (as indicated in the table below) in 0.1M K$_2$HPO$_4$, pH 7.0; 100 μL of a 20 mg/mL solution of glucose dehydrogenase in 0.1M K$_2$HPO$_4$, pH 7.0; and approximately 20 mg of Compound 407 in 50-150 μL of DMSO or MTBE. The sample was shaken or stirred overnight at 30° C. The sample was then extracted with MTBE or EtOAc and analyzed by TLC and certain select samples by chiral GC/HPLC to determine conversion to Compound 421(R) and enantiomeric enrichment. The results are set forth in Table 1.

TABLE 1

Screening of ALMAC Carbonyl Reductases

| Enzyme | Cofactor | Estimated Conversion By TLC | Conversion By HPLC | S/R Ratio of Alcohol |
|---|---|---|---|---|
| A101 | NADP | 10% | N/A | N/A |
| A201 | NADP | 0% | N/A | N/A |
| A301 | NADP | 5% | N/A | N/A |
| A401 | NADP | 10% | N/A | N/A |
| A501 | NADP | 0% | N/A | N/A |
| A601 | NADP | 100% | 99.90% | 0.2/99.8 |
| A701 | NADP | 0% | N/A | N/A |
| A801 | NADP | 20% | 8.20% | 92.4/7.6 |
| A901 | NADP | 50% | 32.10% | 96.5/3.5 |
| A121 | NADP | 10% | N/A | N/A |
| A131 | NAD | 100% | 99.70% | 99.7/0.3 |
| A141 | NADP | 5% | N/A | N/A |
| A151 | NAD | 35% | 20.10% | 35.0/65.0 |
| A161 | NAD | 100% | 99.90% | 2.6/97.4 |
| A171 | NAD | 0% | N/A | N/A |
| A181 | NADP | 10% | N/A | N/A |
| A191 | NAD | 0% | N/A | N/A |
| A211 | NADP | 0% | N/A | N/A |
| A221 | NAD | 0% | N/A | N/A |
| A231 | NADP | 5% | N/A | N/A |
| A241 | NADP | 0% | N/A | N/A |
| A251 | NAD | 100% | 99.90% | 99.9/0.1 |
| A261 | NADP | 0% | N/A | N/A |
| A271 | NADP | 45% | 36.50% | 99.4/0.6 |
| A281 | NADP | 40% | 36.70% | 73.2/26.8 |
| A291 | NADP | 90% | 97.20% | 0.1/99.9 |
| A311 | NADP | 100% | 99.80% | 0.1/99.9 |
| A321 | NADP | 0% | N/A | N/A |
| A331 | NADP | 5% | N/A | N/A |
| A341 | NADP | 10% | N/A | N/A |
| A351 | NADP | 0% | N/A | N/A |
| A361 | NADP | 0% | N/A | N/A |
| A371 | NADP | 50% | 51.60% | 73.0/27.0 |
| A381 | NADP | 0% | N/A | N/A |
| A391 | NADP | 0% | N/A | N/A |
| N501 | NADP | 0% | N/A | N/A |
| N701 | NADP | 0% | N/A | N/A |
| N121 | NADP | 0% | N/A | N/A |
| N131 | NADP | 5% | N/A | N/A |
| N151 | NADP | 10% | N/A | N/A |

The results of this experiment demonstrated that ALMAC Carbonyl Reductase CRED A291, CRED A311, CRED A161, or CRED A601 were useful in the process of this invention.

Codexis Ketoreductases.

The CODEXIS Ketoreductase (KRED) Enzyme Screening Kit contained 34 enzymes that used either NADP (Kit KRED-22000) or NAD (Kit KRED-12000) as a co-factor. The screening Kit KRED-22000 contained 22 KRED-NADP enzymes and their screening test results were carried out according to manufacturer's directions using approximately 5 mg of KRED-NADP enzyme and 71 mg of Compound 407 and the appropriate CODEXIS buffer system (KRED-NADPH Recycle Mix A or KRED-NADH Recycle Mix A) for each reaction. Reactions were tested by TLC (data not shown) and selected reactions were tested by chiral HPLC after 40 hours. These results are set forth in Tables 2 and 3. Results indicated by a dash ("-") indicate an insufficient amount of Compound 421(R) or its stereoisomer were produced by TLC to warrant detection by HPLC.

TABLE 2

Screening of Codexis Ketoreductases in Kit KRED-22000.

| KRED-NADP Enzyme | Conversion By HPLC | S/R Ratio of Alcohol |
| --- | --- | --- |
| KRED-101 | 26.30% | 29.8/70.2 |
| KRED-102 | — | — |
| KRED-103 | — | — |
| KRED-107 | — | — |
| KRED-112 | 23.80% | 27.2/72.8 |
| KRED-113 | — | — |
| KRED-118 | 52.80% | 7.8/92.2 |
| KRED-119 | 99.70% | 91.6/8.4 |
| KRED-121 | — | — |
| KRED-128 | 41.80% | 72.0/28.0 |
| KRED-129 | — | — |
| KRED-130 | 99.50% | 78.7/21.3 |
| KRED-131 | — | — |
| KRED-137 | 25.60% | 96.4/3.6 |
| KRED-140 | — | — |
| KRED-142 | — | — |
| KRED-147 | — | — |
| KRED-148 | 76.70% | 99.5/0.5 |
| KRED-149 | — | — |
| KRED-164 | — | — |
| KRED-169 | 65.10% | 98.9/1.1 |
| KRED-174 | 73.90% | 99.2/0.8 |

TABLE 3

Screening of Codexis Ketoreductases in Kit KRED-12000.

| KRED-NADH Enzyme | Conversion By HPLC | S/R Ratio of Alcohol |
| --- | --- | --- |
| 101 | 100% | 100/0 |
| 102 | 100% | 100/0 |
| 107 | — | — |
| 108 | — | — |
| 109 | — | — |
| 110 | 100% | 1.5/98.5 |
| 112 | 99.90% | 99.8/0.2 |
| 113 | — | — |
| 119 | — | — |
| 121 | — | — |
| 124 | — | — |
| 126 | 100% | >99.9/0.1 |

The above results indicated that CODEXIS Ketoreductases KRED-118 and KRED-NADH 110 were useful in the process of this invention.

Syncore Ketoreductases

SYNCORE Ketoreductase (ES-KRED) Enzyme Screening Kit contained 75 enzymes. Twenty-one ketoreductases (NADH dependent) were tested for the reduction of Compound 407 on 100 mg scale. The CODEXIS buffer system (KRED-NADH Recycle Mix A) was used for these screening tests. The reduction was conducted with 5 wt % of enzyme loading in 50 vol of buffer at 30° C. The reactions were checked by TLC (data not shown) and selected reaction mixtures were checked by chiral HPLC and worked up. Results indicated by a dash ("-") indicate an insufficient amount of Compound 421(R) or its stereoisomer were produced by TLC to warrant detection by HPLC. The results are summarized in Table 4.

TABLE 4

Screening of Syncore NADH-dependent Ketoreductases.

| Enzyme | Conversion By HPLC | S/R Ratio of Alcohol |
| --- | --- | --- |
| ES-KRED-121 | 99.62% | 100/0 |
| ES-KRED-122 | — | |
| ES-KRED-125 | — | |
| ES-KRED-126 | 100.00% | 0/100 |
| ES-KRED-128 | 99.42% | 99.83/0.17 |
| ES-KRED-129 | — | |
| ES-KRED-130 | 100.00% | 100/0 |
| ES-KRED-132 | — | |
| ES-KRED-133 | — | |
| ES-KRED-134 | — | |
| ES-KRED-137 | — | |
| ES-KRED-138 | — | |
| ES-KRED-141 | — | |
| ES-KRED-142 | 100.00% | 100/0 |
| ES-KRED-143 | — | |
| ES-KRED-144 | — | |
| ES-KRED-155 | — | |
| ES-KRED-159 | — | |
| ES-KRED-165 | — | |
| ES-KRED-166 | — | |
| ES-KRED-175 | 22.71% | 100/0 |

The remaining 54 NADPH dependent ketoreductases from Syncore were also tested for the reduction of Compound 407 (100 mg) using the CODEXIS buffer system (KRED-NADPH Recycle Mix A). The reduction was conducted with 5 wt % of enzyme loading in 50 vol of buffer at 30° C. The reactions were checked by TLC (data not shown) and selected reaction mixtures were checked by chiral HPLC and worked up. Results indicated by a dash ("-") indicate an insufficient amount of Compound 421(R) or its stereoisomer were produced by TLC to warrant detection by HPLC. The results are summarized in Table 5.

TABLE 5

Screening of Syncore NADPH-dependent Ketoreductases.

| Enzyme | Conversion By HPLC | S/R Ratio of Alcohol |
| --- | --- | --- |
| ES-KRED-101 | — | — |
| ES-KRED-102 | — | — |
| ES-KRED-103 | — | — |
| ES-KRED-104 | — | — |
| ES-KRED-105 | — | — |
| ES-KRED-106 | — | — |
| ES-KRED-107 | — | — |

TABLE 5-continued

Screening of Syncore NADPH-dependent Ketoreductases.

| Enzyme | Conversion By HPLC | S/R Ratio of Alcohol |
| --- | --- | --- |
| ES-KRED-108 | — | — |
| ES-KRED-109 | — | — |
| ES-KRED-110 | — | — |
| ES-KRED-111 | — | — |
| ES-KRED-112 | — | — |
| ES-KRED-113 | — | — |
| ES-KRED-114 | — | — |
| ES-KRED-115 | — | — |
| ES-KRED-116 | — | — |
| ES-KRED-117 | — | — |
| ES-KRED-118 | — | — |
| ES-KRED-119 | — | — |
| ES-KRED-120 | 99.30% | 0.18/99.82 |
| ES-KRED-123 | — | — |
| ES-KRED-124 | — | — |
| ES-KRED-127 | — | — |
| ES-KRED-131 | 99.90% | 0.06/99.94 |
| ES-KRED-135 | — | — |
| ES-KRED-136 | — | — |
| ES-KRED-139 | — | — |
| ES-KRED-140 | — | — |
| ES-KRED-145 | — | — |
| ES-KRED-146 | — | — |
| ES-KRED-147 | — | — |
| ES-KRED-148 | — | — |
| ES-KRED-149 | — | — |
| ES-KRED-150 | — | — |
| ES-KRED-151 | — | — |
| ES-KRED-152 | — | — |
| ES-KRED-153 | — | — |
| ES-KRED-154 | — | — |
| ES-KRED-156 | — | — |
| ES-KRED-157 | — | — |
| ES-KRED-158 | — | — |
| ES-KRED-160 | — | — |
| ES-KRED-161 | — | — |
| ES-KRED-162 | — | — |
| ES-KRED-163 | — | — |
| ES-KRED-164 | — | — |
| ES-KRED-167 | — | — |
| ES-KRED-168 | — | — |
| ES-KRED-169 | 99.96% | 99.94/0.06 |
| ES-KRED-170 | — | — |
| ES-KRED-171 | 100% | 98.70/1.30 |
| ES-KRED-172 | — | — |
| ES-KRED-173 | — | — |
| ES-KRED-174 | — | — |

From the above experiments, it was determined that SYNCORE Ketoreductases ES-KRED-120, ES-KRED-126, and ES-KRED-131 were suitable for use in the present invention.

Example 3

Preparation of Compound 437(R) from Compound 407 Using CRED-A311 and Deuterated Glucose Generated In Situ

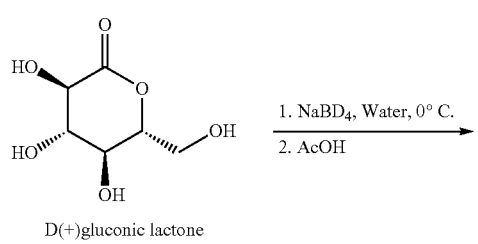

D(+)gluconic lactone

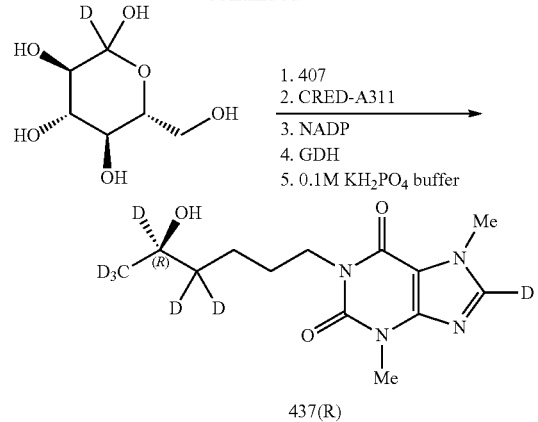

437(R)

a) In Situ Generation of Deuterated Glucose:

Deuterated glucose (D-[1-$^2$H$_1$] Glucose) was prepared according to the procedure described in *Liebigs Ann. Chem.* 1992, 1201-1203. D-Glucono-δ-lactone (5 g, 28.09 mmoles) was added in one portion to ice-cold water (35 mL, 0-3° C.) and stirred for 10 min. A freshly prepared, ice-cold solution of NaBD$_4$ (0.294 g, 7.02 mmoles, 99% D) in 10 mL of water was added slowly during 10 min. The reaction is slightly exothermic (2° to 10° C.) and the pH of the reaction was 7.42. Stirring was continued for 30 min, keeping the temperature by cooling to 0-3° C. Acetic acid (0.32 mL, 5.61 mmoles) was added and stirring was continued further 30 min.

b) Preparation of Compound 437(R) from Compound 407:

The reaction mixture obtained in step (a) was diluted with 18 ml of water and the solution was heated to 25-30° C. KH$_2$PO$_4$ (0.85 g) was added to the mixture and the pH was adjusted to 7 with 4M KOH solution. To this was added 2.5 g (8.8 mmoles) of 407. A solution of NADP (15 mg), GDH (2.5 mg), CRED A311 (25 mg) in 12.5 mL of 0.1 KH$_2$PO$_4$ buffer was added. The resulting solution was stirred at 25-30° C. The pH of the reaction mixture was maintained between 6 and 7 by adding 4M KOH solution drop-wise. The reaction was monitored by HPLC and was complete after 12 hours with 99.97% conversion by HPLC. Sodium chloride (12.5 g) was added and stirred for 30 min. The mixture was extracted with ethyl acetate (3×25 mL). The organic layer was separated, filtered through celite pad and concentrated to a small volume (~5 vol) and product solids were precipitated. Heptanes (20 mL) were added to the slurry (at 40-60° C.) over 10 minutes. The slurry was stirred overnight at 20-25° C. and filtered. The wet cake was dried at 50° C. for 12 hours to afford 437(R) as a white solid. (2.12 g, 85% yield). The isolated product purity was >99.95% by HPLC and as a single enantiomer by chiral HPLC.

Compound 437 (R) may be further converted to Compound 137(R) by treatment with K$_2$CO$_3$ and water, as follows:

Preparation of Compound 137(R) from Compound 437(R).

In a 3-L 3-necked RB flask, Compound 437(R) (100 g) was charged followed by water (1.0 L) and K$_2$CO$_3$ (0.25 equiv). The reaction mixture was heated to 80±5° C. and monitored by $^1$H NMR. The reaction was complete after 24 hours and worked up after 65 hours. The resulting product was extracted with three times with EtOAc and the solid products from the three extractions combined and re-dissolved in 5 volumes of EtOAc at 60-65° C. n-heptane (5.5 vol.) was added at 60-65° C. over 15 minutes and cooled to 20° C. over night (16 hrs). The slurry was filtered and the wet cake was washed with n-heptane (2×1 vol. to afford product Compound 137(R) after drying at 40-50° C. A total of 92.4 g of Compound 137(R) was isolated. HPLC purity was 99.92% (AUC) and chiral selectivity was 100% to "S" enantiomer. The $^1$H NMR analysis showed 99.2% of "H" at the 8-position in the 3,4,5,7-tetrahydro-1H-purine-2,6-dione ring and 99.4% of "D" at the methyl position.

Example 4

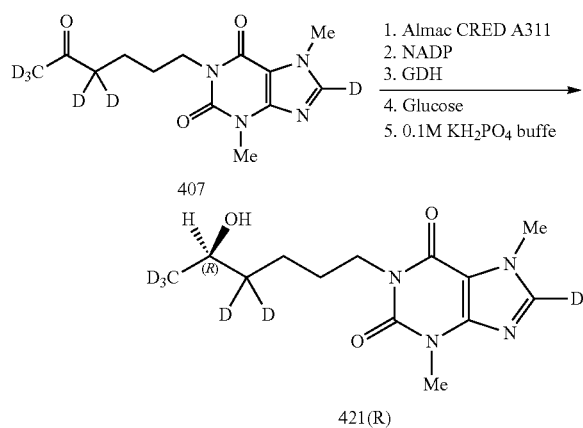

Preparation of Compound 421(R) from Compound 407 Using CRED A131

A 100 mL 3-necked RB flask equipped with a heating mantle, a J-Kem thermocouple, magnetic stir bar, a reflux condenser, and a pH probe was charged with CTP-499-A (500 mg, 1.75 mmol), D(+) Glucose (750 mg, 1.5 wt) in 10 mL buffer (0.1M $KH_2PO_4$, pH=7.0) and heated to 25-30° C. A solution of NADP (15 mg, 3 wt %), GDH (3 mg, 0.6 wt %), ALMAC CRED A311 (30 mg, 6 wt %) in 0.1 M $KH_2PO_4$ buffer was added and maintained reaction temperature 25-30° C.

To this added 1 mL of methyl-t-butyl ether (MTBE). The pH of the reaction mixture was maintained between 6 and 7 adding 4M KOH solution drop-wise. The reaction was monitored by HPLC and was complete after 29 hours with 99.87A % conversion by HPLC. Sodium chloride (2.5 g, 5 wt) was added and stirred for 20 min. The reaction mixture was extracted with ethyl acetate (3×15 mL). The organic layer was separated, filtered through celite pad and concentrated to a small volume (~5 vol) and product solids were precipitated. Heptanes (5 mL) was added to the slurry (at 40-60° C.) over 5 minutes. The slurry was stirred at 20-25° C. and filtered. The wet cake was dried at 50° C. for 12 hours to afford CTP-499-G as a white solid. (0.422 g, 84% yield). The isolated product purity was >99.5% by HPLC and single enantiomer by chiral HPLC.

What is claimed is:

1. A process for the preparation of a compound of Formula I-A

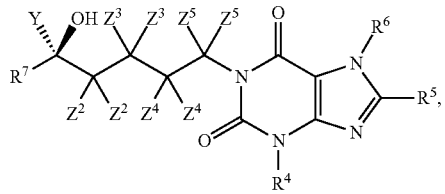

comprising the step of reacting a compound of Formula II-A:

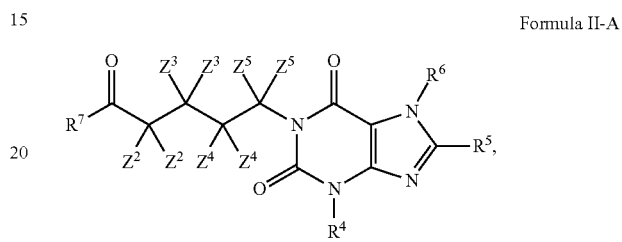

or a salt thereof, with a hydride source or a deuteride source in the presence of a ketoreductase or carbonyl reductase to form a compound of Formula I-A with an enantiomeric excess of at least 80%, wherein:

the ketoreductase or carbonyl reductase is selected from CRED A161, CRED A291, CRED A311, CRED A601 KRED-NADP-118, KRED-NADH-110, ES-KRED-120, ES-KRED-126, and ES-KRED-131;

each of $R^4$, $R^6$ and $R^7$ is independently selected from —$CH_3$ and —$CD_3$;

each $R^5$ is hydrogen or deuterium or a combination thereof;

each $Z^2$ is the same and is hydrogen or deuterium;

each $Z^3$ is the same and is hydrogen or deuterium;

each $Z^4$ is the same and is hydrogen or deuterium;

each $Z^5$ is the same and is hydrogen or deuterium; and

Y is H when a compound of Formula II-A is reacted with a hydride source; or

Y is D when a compound of Formula II-A is reacted with a deuteride source, wherein either $R^7$ is —$CD_3$ or at least one of $Z^2$, $Z^3$, $Z^4$ and $Z^5$ is deuterium, and wherein the amount of deuterium incorporation at each deuterium in $R^7$, $Z^2$, $Z^3$, $Z^4$ and $Z^5$ in the compound of Formula I-A is substantially equal to the amount of deuterium incorporation at corresponding deuterium atoms in $R^7$, $Z^2$, $Z^3$, $Z^4$ and $Z^5$ in the compound of Formula II-A.

2. The process of claim 1, wherein each $R^7$ is —$CD_3$.

3. The process of claim 1, wherein each $Z^2$ is deuterium.

4. The process of claim 1, wherein each $Z^2$ is hydrogen.

5. The process of claim 1, wherein each $R^5$ is deuterium.

6. The process of claim 1, wherein each $R^5$ is hydrogen.

7. The process of claim 1, wherein each $Z^3$, $Z^4$ and $Z^5$ is hydrogen.

8. The process of claim 7, wherein $R^6$ is —$CH_3$ and $R^7$ is —$CD_3$.

9. The process of claim 8, wherein $R^4$ is —$CH_3$.

10. The process of claim 7, wherein $R^6$ is —$CD_3$ and $R^7$ is —$CD_3$.

11. The process of claim 1, wherein each $Z^3$, $Z^4$ and $Z^5$ is deuterium.

12. The process of claim 11, wherein each $R^6$ and each $R^4$ is —$CD_3$.

13. The process of claim 1, wherein:
a. the compound of Formula II-A is selected from any one of the following:
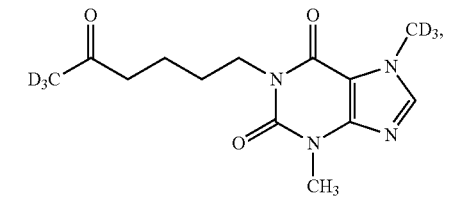
99
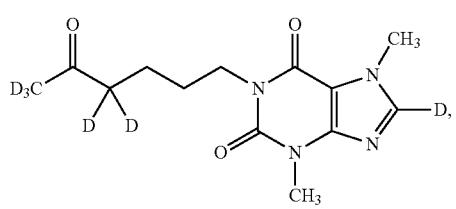
407
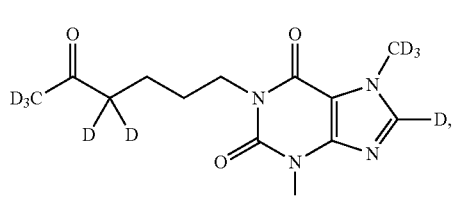
409
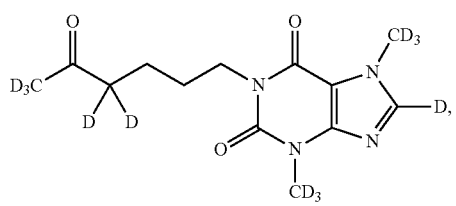
413
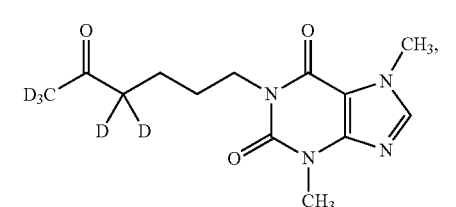
107
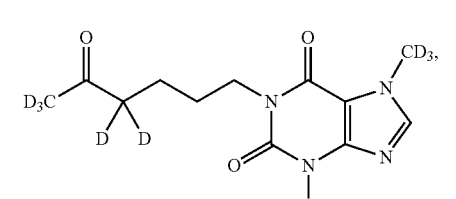
109
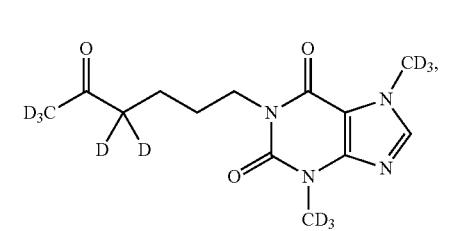
113
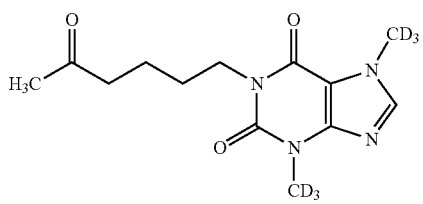
101
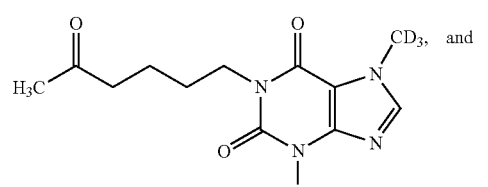
100 and
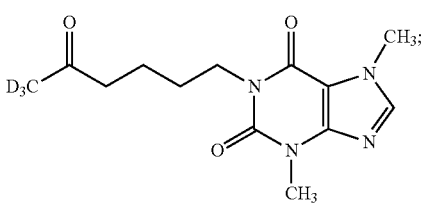
157
and
b. the compound of Formula I-A is selected from any one of the following
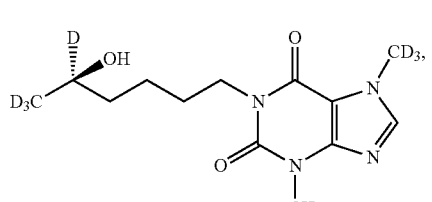
154(R)
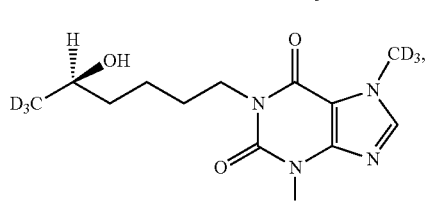
155(R)
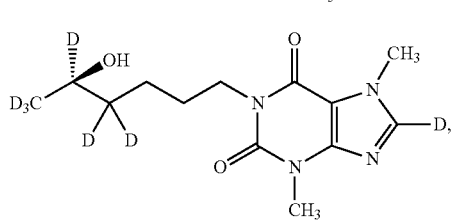
437(R)
421(R)

25
-continued
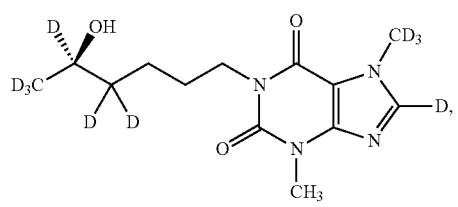
435(R)
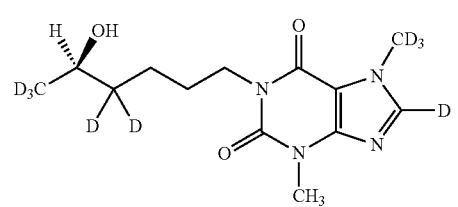
419(R)
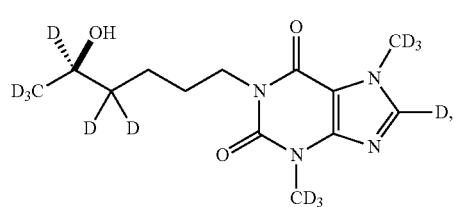
434(R)
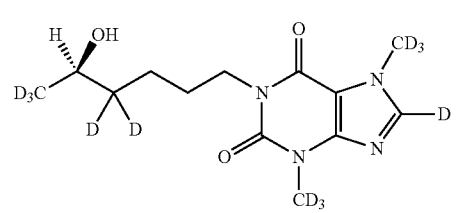
418(R)
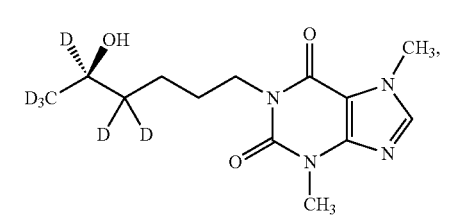
137(R)
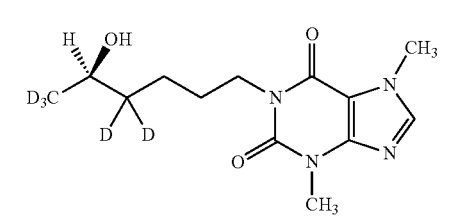
121(R)
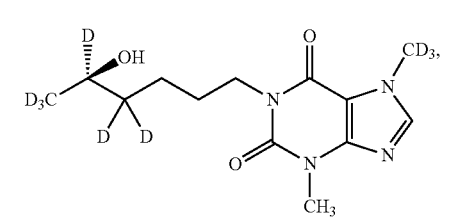
135(R)
26
-continued
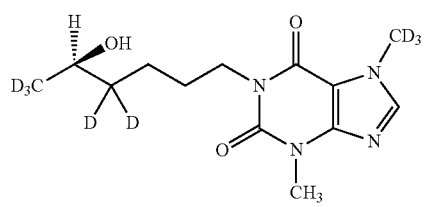
119(R)
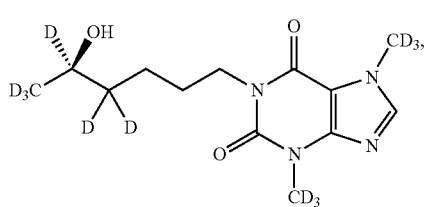
134(R)
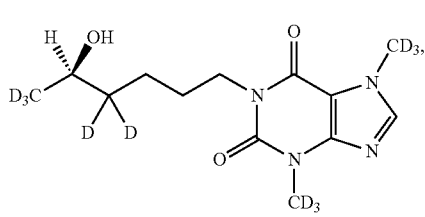
118(R)
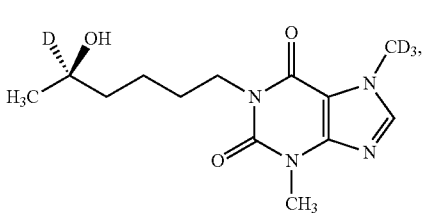
131 (R)
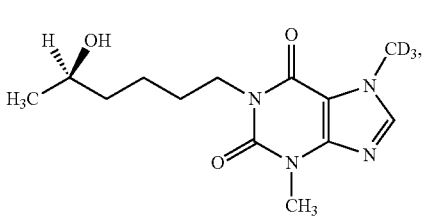
116 (R)
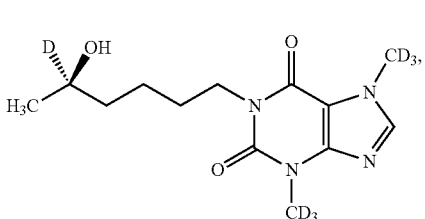
130 (R)
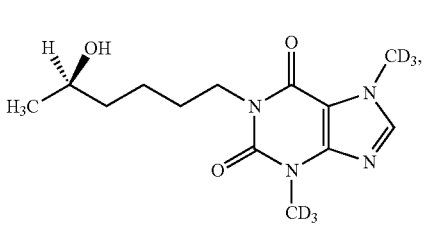
115 (R)

-continued

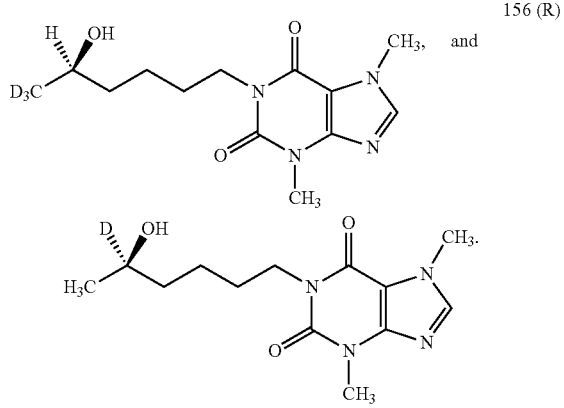

156 (R)

and

14. The process of claim 1, wherein:

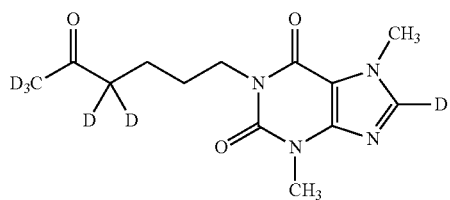

407 the compound of Formula II-A is (Compound 407); and

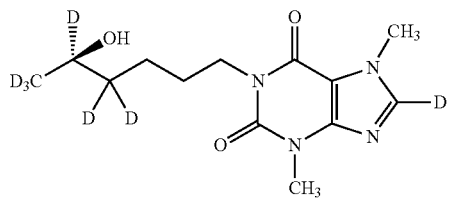

437(R)

the compound of Formula I-A is (Compound 437(R)).

15. The process of claim 13, wherein the compound of Formula I-A is Compound 421(R), and further comprising the step of converting Compound 421(R) to Compound 121 (R):

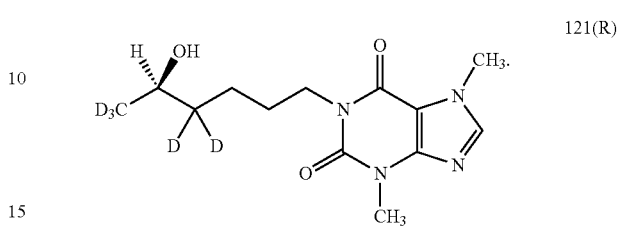

121(R)

16. The process of claim 1, wherein the hydride source or deuteride source is (i) a cofactor selected from NAD, NADH, NADP and NADPH, (ii) a reducing sugar and (iii) a dehydrogenase that dehydrogenates the reducing sugar.

17. The process of claim 16, wherein Y is H; and the hydride source is (i) a cofactor selected from NAD, NADH, NADP and NADPH, (ii) glucose and (iii) glucose dehydrogenase.

18. The process of claim 16, wherein Y is D; and the deuteride source is (i) a cofactor selected from NAD and NADP, (ii) deuterated glucose, and (iii) glucose dehydrogenase.

19. The process of claim 18, wherein the deuterated glucose is generated from (i) D-glucono-δ-lactone and (ii) a metal deuteride or a mixed metal deuteride.

20. The process of claim 19, wherein the metal deuteride or mixed metal deuteride is $NaBD_4$.

21. The process of claim 1, wherein the step of reacting a compound of Formula II-A or a salt thereof with a hydride source or a deuteride source is performed at a pH between 6.0 and 7.5.

22. The process of claim 21, wherein the pH is between 6.90 and 7.05.

23. The process of claim 1, wherein the ketoreductase or carbonyl reductase is CRED A311.

* * * * *